United States Patent [19]

Haneishi et al.

[11] Patent Number: 4,918,054

[45] Date of Patent: Apr. 17, 1990

[54] ANTIBIOTICS CALLED 'CHLOROPOLYSPORINS B AND C', A PROCESS FOR THEIR PREPARATION, AND THEIR THERAPEUTIC AND VETERINARY USE

[75] Inventors: Tatsuo Haneishi; Takao Okazaki; Akio Torikata; Mutsuo Nakajima; Ryuzo Enokita; Toshiaki Katayama; Seigo Iwado, all of Hiromachi, Japan

[73] Assignee: Sankyo Company Limited, Tokyo, Japan

[21] Appl. No.: 379,656

[22] Filed: Jul. 11, 1989

Related U.S. Application Data

[63] Continuation of Ser. No. 813,617, Dec. 26, 1985, abandoned.

[30] Foreign Application Priority Data

Jan. 11, 1985 [JP] Japan .................................. 60-2805

[51] Int. Cl.$^4$ ..................... A61K 35/74; A61K 37/02; C07K 7/50; C07K 9/00
[52] U.S. Cl. ............................................ 514/8; 514/9; 530/317; 530/322; 424/117; 424/118
[58] Field of Search ............... 514/8, 9; 530/317, 321, 530/322; 424/117, 118

[56] References Cited

U.S. PATENT DOCUMENTS 4,557,933 12/1985 Haneishi et al. .................... 424/118

OTHER PUBLICATIONS

Takatsu et al., The Journal of Antibiotics, vol. 40, No. 7, pp. 946–952 (7/87).
Okazaki et al., The Journal of Antibiotics, vol. 40, No. 7, pp. 917–923 (7/87).
Takatsu et al., The Journal of Antibiotics, vol. 40, No. 7, pp. 924–932 (7/87).
Takatsu et al., The Journal of Antibiotics, vol. 40, No. 7, pp. 933–940 (7/87).
Takatsu et al., The Journal of Antibiotics, vol. 40, No. 7, pp. 941–945 (7/87).

Primary Examiner—Lester L. Lee
Assistant Examiner—Christina Chan
Attorney, Agent, or Firm—Frishauf, Holtz, Goodman & Woodward

[57] ABSTRACT

Novel compounds, called chloropolysporins B and C, and salts thereof have antibiotic properties and would appear to be members of the class of glycopeptide antibiotics containing chlorine. They may be produced by cultivating a suitable strain of miroorganism of the genus Micropolyspora, especially Micropolyspora sp. SANK 60983 (FERM BP-538). They may be combined with conventional pharmaceutically acceptable carriers or diluents for therapeutic use or incorporated into edible excipients, such as feed or water, for use as a growth-promoting agent, especially for farm animals.

6 Claims, 6 Drawing Sheets

ANTIBIOTICS CALLED 'CHLOROPOLYSPORINS B AND C', A PROCESS FOR THEIR PREPARATION, AND THEIR THERAPEUTIC AND VETERINARY USE

This application is a continuation of application Ser. No. 06/813,617, filed Dec. 26, 1985 now abandoned.

BACKGROUND TO THE INVENTION

The present invention relates to new antibiotics, which we have called "chloropolysporins B and C", to a process for their preparation by the cultivation of a microorganism and to their use, both therapeutic, in the treatment and prophylaxis of infections caused by bacteria, and as a growth-promoting agent for animals.

As resistance to conventional antibiotics becomes increasingly established in common strains of pathogenic bacteria, the need for a wider variety of antibiotics for use in the fight against such bacteria becomes ever more crucial. Moreover, various antibiotics, for example chloramphenicol, aureomycin, vancomycin and avoparcin, have been administered, or have been proposed for administration, to poultry and other farm animals, including the ruminants and pigs, for the prophylaxis of disease or to promote growth or milk production. However, an inherent disadvantage of the use of antibiotics in this way is that there is some risk that traces of the antibiotics or of metabolic products thereof may be found in animal products intended for human consumption (such as eggs, milk or meat); the alleged dangers of such residues are increasingly criticized by some sections of the community. There is, accordingly, a considerable desire amongst farmers for an antibiotic substance which will leave the desired growth-promoting effect but which will leave no or no significant residues in animal products.

In U.S. patent application Ser. No. 627,439, filed July 3rd 1984, which issued as U.S. Pat. No. 4,557,933, on Dec. 10, 1985, assigned to the present assignees, there is disclosed an antibiotic, there referred to as "chloropolysporin", which was isolated from the culture medium of a microorganism identified as Micropolyspora sp. SANK 60983.

We have now discovered that the same microorganism, and hence others of the genus Micropolyspora, produces a further two new antibiotic substances that are highly effective against gram-positive bacteria and that show considerable promise for use as growth-promoting agents in animals. It is believed that these substances may have been present in the chloropolysporin of the prior Application.

BRIEF SUMMARY OF INVENTION

The new antibiotic substances of the invention are called "chloropolysporin B" and "chloropolysporin C" and, since their structures have not been completely elucidated, they may be characterized by their properties.

Chloropolysporin B, as its sulfate, is characterized by the properties:

(a) it takes the form of an amphoteric white powder, soluble in water;

(b) specific rotation: $[\alpha]^{25} -64.5°$ (C=1.04, 0.1N aqueous hydrochloric acid, sodium D-line);

(c) elemental analysis: C, 48.33%; H, 5.05%; N, 5.48%; Cl, 5.11%; S, 1.00%;

(d) on acid hydrolysis it yields: neutral saccharides: glucose, mannose and rhamnose; amino acids: 3-chloro-4-hydroxyphenylglycine and N-methyl-p-hydroxyphenylglycine;

(e) ultraviolet absorption spectrum: as illustrated FIG. 1 of the accompanying drawings, having an absorption maximum $\lambda_{max}$ at 280nm ($E_{1cm}=51$) in a 0.1 N solution of hydrochloric acid, the absorbence, E, being measured at a concentration of 1% w/v;

(f) infrared absorption spectrum: the infrared absorption spectrum ($\nu$ cm$^{-1}$) measured on a KBr disc is as shown in FIG. 2 of the accompanying drawings;

(g) nuclear magnetic resonance spectrum: the nuclear magnetic resonance spectrum ($\delta$ ppm), measured at 270 MHz in deuterated dimethyl sulfoxide using tetramethylsilane as the internal standard, is as illustrated in FIG. 3 of the accompanying drawings;

(h) solubility: soluble in water and methanol, sparingly soluble in acetone, and insoluble in ethyl acetate, chloroform and benzene;

(i) color reactions: positive in Ninhydrin and Rydon-Smith reactions;

(j) thin layer chromatography: Rf value=0.65, using a cellulose sheet (Eastman) as adsorbent and a 15:10:3:12 by volume mixture of butanol, pyridine, acetic acid and water as the developing solvent;

(k) high voltage paper electrophoresis: using Toyo's filter paper No. 51A in a 0.1M tris-hydrochloric acid buffer solution of pH 7.5 (3300 volt/60 cm, 1 hour); the migration distance (detected by bioautography with Bacillus subtilis PCI 219) from the origin to the cathode was 4 cm;

(l) molecular formula: $C_{83}H_{89}O_{34}N_8Cl_3 \cdot 0.5H_2SO_4 \cdot 10H_2O$;

(m) molecular weight: the molecular weight, measured by FAB-MS, was 1846 (MH$^+$, 1847).

"FAB-MS" is Fast Atom Bombardment Mass Spectroscopy. Chloropolysporin C, as its sulfate, may be characterized by the following properties:

(a) it takes the form of an amphoteric white powder, soluble in water;

(b) specific rotation: $[\alpha]^{25} -64.4°$ (C=1.08, 0.1N aqueous hydrochloric acid, sodium D-line);

(c) elemental analysis: C, 50.53%; H, 4.69%; N, 6.14%; Cl, 5.62%; S, 1.12%;

(d) on acid hydrolysis it yields: neutral saccharides: glucose and mannose; amino acids: 3-chloro-4-hydroxphenylglycine and N-methyl-p-hydroxyphenylglycine;

(e) ultraviolet absorption spectrum: as illustrated FIG. 4 of the accompanying drawings, having an absorption maximum $\lambda_{max}$ at 280nm ($E_{1cm}=57$) in a 0.1 N solution of hydrochloric acid, the absorbence, E, being measured at a concentration of 1% w/v;

(f) infrared absorption spectrum: the infrared absorption spectrum ($\nu$cm$^{-1}$) measured on a KBr disc is as shown in FIG. 5 of the accompanying drawings;

(g) nuclear magnetic resonance spectrum: the nuclear magnetic resonance spectrum ($\delta$ ppm), measured at 400 MHz in deuterated dimethyl sulfoxide using tetramethylsilane as the internal standard, is as illustrated in FIG. 6 of the accompanying drawings;

(h) solubility: soluble in water and methanol, sparingly soluble in acetone, and insoluble in ethyl acetate, chloroform and benzene;

(i) color reactions: positive in Ninhydrin and Rydon-Smith reactions;

(j) thin layer chromatography: Rf value=0.65, using a cellulose sheet (Eastman) as adsorbent and a 15:10:3:12 by volume mixture of butanol, pyridine, acetic acid and water as the developing solvent;

(k) molecular formula: $C_{77}H_{79}O_{30}N_8Cl_3 \cdot 0.5H_2SO_4 \cdot 5H_2O$;

(l) molecular weight: the molecular weight, measured by FAB-MS, was 1700 (MH+, 1701).

The present invention provides these compounds for the first time in a form suitable for medicinal or veterinary use, free from native impurities.

The invention also provides pharmaceutically acceptable salts of these compounds.

The invention also provides a process for producing chloropolysporin B or chloropolysporin C and salts thereof by cultivating a chloropolysporin B- or C-producing microorganism of the genus Micropolyspora in a culture medium therefor and isolating chloropolysporin B or C or a salt thereof from the cultured broth.

The invention still further provides a pharmaceutical or veterinary composition comprising such chloropolysporin B or C or a salt thereof in admixture with a pharmaceutical or veterinary carrier or diluent.

The invention still further provides a method for the treatment or prophylaxis of bacterial infections by administering such chloropolysporin B or C or a salt thereof to an animal, which may be human or non-human.

The invention still further provides a method of promoting the growth of a farm animal by the oral administration of such chloropolysporin B or C or a salt thereof to said animal.

DETAILED DESCRIPTION OF INVENTION

Figure 1:
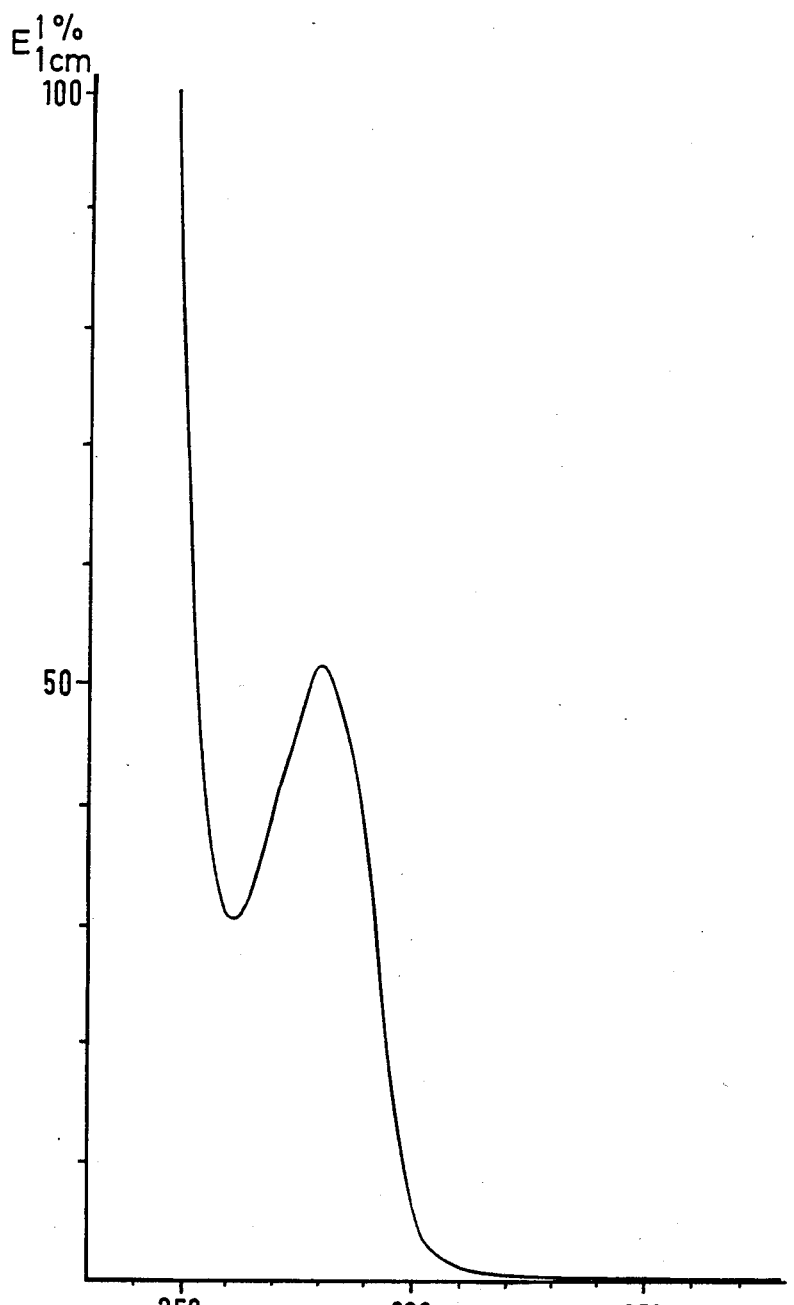
FIG. 1 is the ultraviolet absorption spectrum of chloropolysporin B of the invention.
Figure 2:
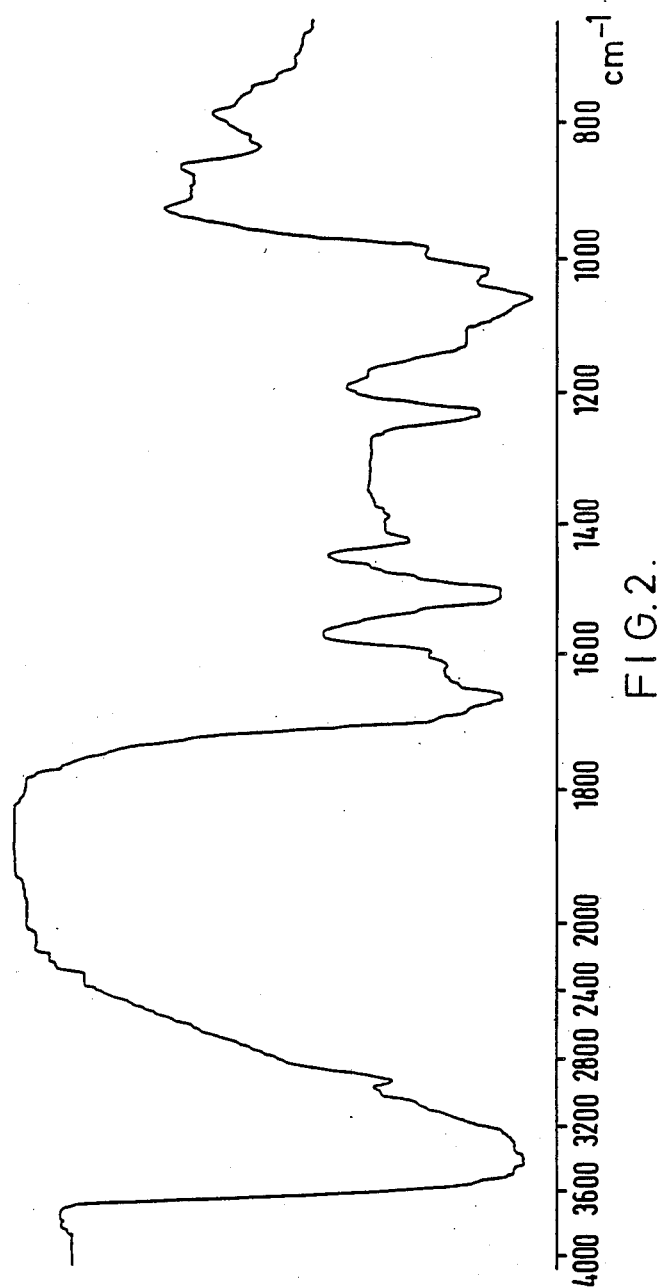
FIG. 2 is the infrared absorption spectrum of chloropolysporin B of the invention.
Figure 3:
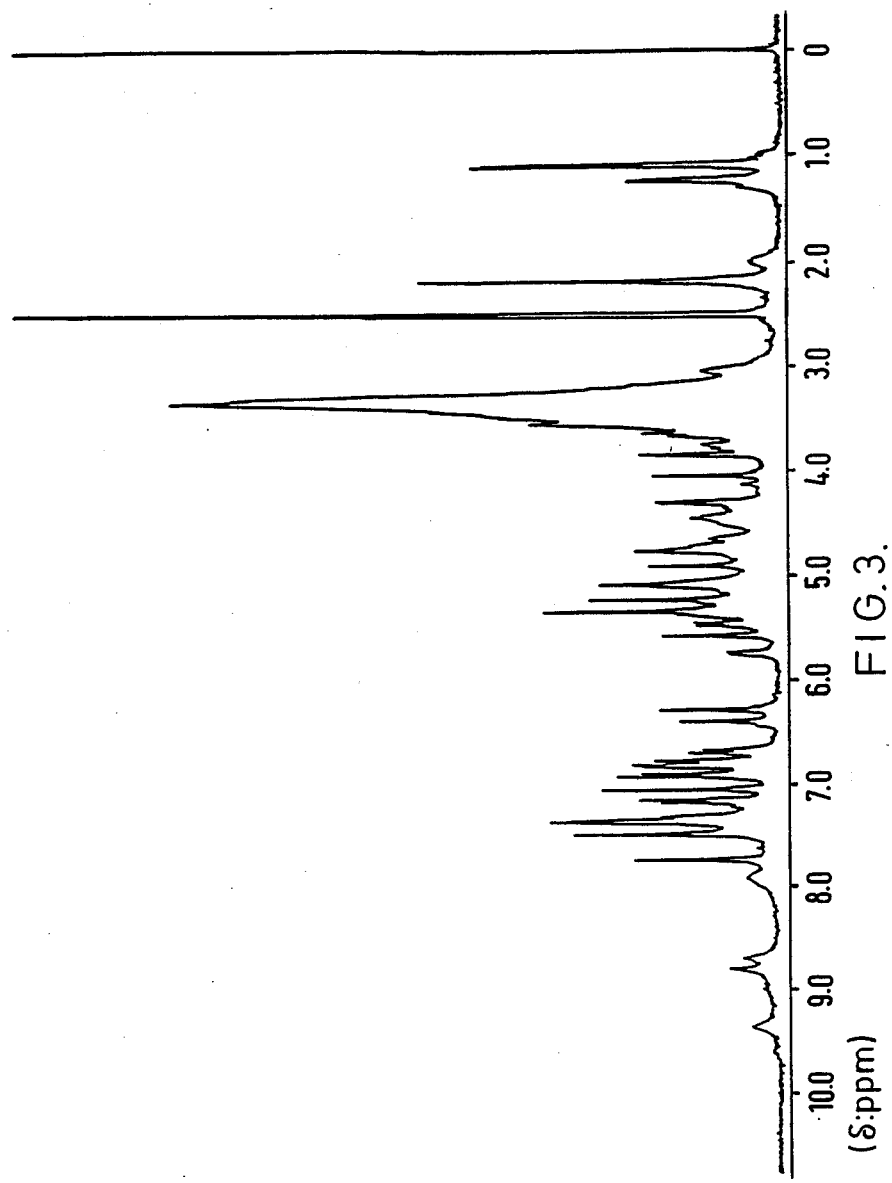
FIG. 3 is the NMR spectrum of chloropolysporin B of the invention.

The invention is based upon the discovery and isolation of chloropolysporin B and chloropolysporin C and salts thereof, each free from contamination by other products of cell metabolism, and preferably free from each other.

Chloropolysporins B and C are produced by the cultivation of a Micropolyspora strain herein identified as Micropolyspora sp. SANK 60983, which was isolated from a soil sample collected in Tochigi Prefecture, Japan.

The microorganism, Micropolyspora SANK 60983, has the characteristics described hereafter and is as described in U.S. patent application Ser. No. 627,439, referred to above. These characteristics were determined by cultivation on various media prescribed by the ISP (International Streptomyces Project) or with the media recommended by S.A. Waksman in Volume 2 of "The Actinomycetes", in all cases at a temperature of 28° C.

1. Morphological Characteristics

Strain SANK 60983 grows relatively well on various media. The aerial mycelium is hardly visible on almost all media but may occasionally be visible on glycerol-asparagine agar or on potato extract-carrot extract agar. The aerial and vegetative mycelia bear, at the top and the middle, short chains of spores, normally from 1 to 20, although occasionally more than 20, spores. No distinct fragmentation of the hyphae is observed with the strain, although it may be observed during later stages of the culture.

2. Culture Characteristics

Strain SANK 60983 can produce pale yellow, yellowish brown or yellowish gray colors. Aerial hyphae are not observed on most media, although white aerial hyphae are produced on some media. No soluble pigment is produced. Table 1 shows the results obtained after cultivation for 14 days at 28° C. on various standard culture media. The color names and numbers used were assigned according to the "Guide to Color Standard", a manual published by Nippon Shikisai Kenkyusho, Tokyo, Japan.

TABLE 1

| Medium | Growth | Aerial Mycelium | Reverse | Soluble Pigment |
|---|---|---|---|---|
| Yeast extract-malt extract agar (ISP 2) | Abundant, raised, wrinkled, yellowish-brown (8-8-8) | None | Yellowish-brown (8-8-8) | None |
| Oatmeal agar (ISP 3) | Good, smooth, dull yellow (8-8-9) | None | Dull yellow (8-8-9) | None |
| Inorganic salt-starch agar (ISP 4) | Abundant, smooth, yellowish-gray (2-9-10) to pale yellowish-brown (6-8-9) | None | Yellowish-gray (2-9-10) to pale yellowish-brown (6-8-9) | None |
| Glycerol-asparagine agar (ISP 5) | Good, wrinkled, yellowish-brown (2-9-10) | Poor, white | Yellowish-brown (2-9-10) | None |
| Peptone-yeast extract-iron agar (ISP 6) | Moderate, smooth, pale yellowish-brown (2-8-9) | None | Pale yellowish-brown (4-8-9) | None |
| Tyrosine agar (ISP 7) | Abundant, raised, wrinkled, pale yellowish-brown (14-8-9) | None | Dull yellow (10-8-8) | None |
| Sucrose nitrate agar | Abundant, raised, wrinkled, pale yellow (12-8-10) | None | Pale yellowish-brown (4-8-8) | None |
| Glucose-asparagine agar | Moderate smooth, yellowish-gray (2-9-10) | None | Yellowish-gray (2-9-10) | None |
| Nutrient agar (Difco) | Moderate smooth, pale yellowish-brown (6-8-9) | None | Pale yellowish-brown (6-8-9) | None |

TABLE 1-continued

| Medium | Growth | Aerial Mycelium | Reverse | Soluble Pigment |
|---|---|---|---|---|
| Water agar | Poor, smooth, yellowish-gray (1-9-10) | None | Yellowish-gray (1-9-10) | None |
| Potato extract-carrot extract agar | Moderate smooth, yellowish-gray (2-9-10) | Poor, white | Yellowish-gray (2-9-10) | None |

3. Physiological Properties.

The physiological properties of strain SANK 60983 are shown in Table 2.

TABLE 2

| | | |
|---|---|---|
| Decomposition: | Adenine | − |
| | Casein | + |
| | Xanthine | − |
| | Hypoxanthine | + |
| | Urea | + |
| Hydrolysis of starch | | ± |
| Liquefaction of gelatin | | + |
| Coagulation of milk | | − |
| Peptonization of milk | | − |
| Reduction of nitrate | | + |
| Secretion of deoxyribonuclease | | + |
| Melanin formation: | ISP 1 | − |
| | ISP 6 | − |
| | ISP 7 | − |
| Acid production from: | Sodium Acetate | − |
| | Sodium Succinate | − |
| | Sodium Citrate | − |
| | Sodium Pyruvate | − |
| | Sodium Tartarate | − |
| | D-Glucose | + |
| | L-Arabinose | + |
| | D-Xylose | + |
| | Inositol | + |
| | D-Mannitol | + |
| | D-Fructose | + |
| | L-Rhamnose | + |
| | Sucrose | + |
| | Raffinose | ± |
| Utilization of carbon sources: | D-Glucose | + |
| | L-Arabinose | + |
| | D-Xylose | + |
| | Inositol | + |
| | D-Mannitol | + |
| | D-Fructose | + |
| | L-Rhamnose | + |
| | Sucrose | + |
| | Raffinose | ± |
| Growth in NaCl: | 3% w/v | + |
| | 5% w/v | ± |
| | 7% w/v | ± |
| | 10% w/v | − |
| Range of growth temperature: | 10° C. | − |
| | 20° C. | + |
| | 28° C. | + |
| | 37° C. | + |
| | 45° C. | − |

In the above Table, "+" means positive, "−" means negative and "±" means slightly positive.

Although coagulation and peptonization of milk are both reported as negative, they may occasionally turn positive after long-term culture.

4. Whole Cell Components

Acid hydrolyzates of bacterial cells were assayed by paper chromatography, using the method of M.P. Lechevalier et al. ["The Actinomycetes Taxonomy", page 225 (1980)]. meso-Diaminopimelic acid, arabinose and galactose were found to be present in the cell walls, which are thus of Type IV, whilst the whole cell sugar pattern is of Type A. The characteristic acyl group of the cell wall was also investigated by the method of Uchida et al. [J. Gen. Appl. Microbiol, 23,249 (1977)] and found to be the acetyl group.

None of the known genera of actinomycetes has been reported to be capable of forming spores in the middle of the hyphae. However, from a comparison of other characteristics, the new strain is clearly related to the genera Actinopolyspora, Saccharopolyspora, Pseudonocardia and Micropolyspora. However, both Actinopolyspora and Saccharopolyspora allow spores to grow only on the tips of aerial hyphae, and the former is a highly halophilic genus, whilst the characteristic acyl group of the cell wall of the latter is the glycolyl group. For these reasons, the new strain SANK 60983 cannot be assigned to either of these genera. Although strains of the genus Pseudonocardia can grow spores on the aerial hyphae and on the vegetative mycelium, as does strain SANK 60983, the site of its growth takes place only at the tip of the hyphae and, moreover, its hyphae characteristically grow by budding; thus, strain SANK 60983 cannot be assigned to the genus Pseudonocardia.

The only difference between the genus Micropolyspora and strain SANK 60983 is that the site of growth of spores of Micropolyspora is limited to the tips of the hyphae, whereas that of SANK 60983 is at both the tip and the middle of the hyphae.

At the present time, when there has been virtually no discussion in learned circles as to the implications for taxonomy of differences of this type, it would seem inappropriate to differentiate between genera solely on the basis of differences in the site of growth of their spores. Accordingly, it seems most satisfactory to regard the strain SANK 60983 as representative of a new species of the genus Micropolyspora and it has, accordingly, been named Micropolyspora sp. SANK 60983. It should, however, be remembered that assignment of a strain of microorganism to any particular species, genus or even family is largely a matter of consensus amongst those experienced in the study of the particular class of microorganism involved and the original assignment of a microorganism can be, and not infrequently is, changed after wider discussion.

The strain SANK 60983 has been deposited with the Fermentation Research Institute, Agency of Industrial Science and Technology, Ministry of International Trade and Industry, Japan, on Mar. 10th 1983 under the accession No. FERM P-6985 and was re-deposited in accordance with the conditions stipulated by the Budapest Treaty with said Fermentation Research Institute on June 8th 1984 under the accession No. FERM BP-538.

It has been established that strain SANK 60983 produces chloropolysporins B and C. However, as is well known, the properties of microorganisms falling within the general category of the actinomycetes can vary considerably and such microorganisms can readily undergo mutation, both through natural causes and as the result of induction by artificial means. Accordingly, the process of the present invention embraces the use of any microorganism which can be classified within the genus Micropolyspora and which shares with the strain SANK 60983 the characteristic ability to produce chloropolysporins B and C.

The cultivation of microorganisms of the genus Micropolyspora in accordance with the present invention to produce chloropolysporins B and C can be performed under conditions conventionally employed for the cultivation of actinomycete species, preferably in a liquid culture, and desirably with shaking or stirring and aeration. The nutrient medium used for the cultivation is completely conventional and contains such constituents as are commonly used in the cultivation of the actinomycetes. Specifically, the medium should contain an assimilable carbon source, suitable examples of which include glucose, maltose, sucrose, mannitol, molasses, glycerol, dextrin, starch, soybean oil and cottonseed oil; an assimilable nitrogen source, suitable examples of which include soybean meal, peanut meal, cottonseed meal, fish meal, corn steep liquor, peptone, meat extract, pressed yeast, yeast extract, sodium nitrate, ammonium nitrate or ammonium sulfate; and one or more inorganic salts, such as sodium chloride, phosphates, calcium carbonate and trace metal salts. Where cultivation is effected in a liquid medium, it is generally desirable to incorporate an anti-foaming agent (for example silicone oil, vegetable oil or a suitable surfactant) in the medium.

The cultivation is suitably performed at a substantially neutral pH value and at a temperature of from 24° to 30° C., more preferably at about 28° C.

The production of chloropolysporins B and C as cultivation proceeds may be monitored by a variety of conventional microbiological assay techniques for monitoring the production of antibiotics (when they are produced by microbial culture) and which require little or no elaboration here. A suitable technique might be the paper disc-agar diffusion assay (using, for example, a paper disc of diameter about 8 mm produced by Toyo Kagaku Sangyo Co., Ltd) and using, for example, *Bacillus subtilis* PCI 219 or *Staphylococcus aureus* FDA 209P JC-1 as the test organism.

The amount of chloropolysporins B and C produced normally reaches a maximum after cultivation has proceeded for 55–70 hours and it is clearly desirable to separate the chloropolysporins from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g. as described above.

Chloropolysporins B and C are mainly released into the liquid portion of the cultured broth and can thus be recovered by removing solid matter, including the mycelium, for example by filtration (preferably using a filter aid such as diatomaceous earth) or by centrifugation. It can then be recovered from the separated liquid portion by conventional techniques and, if desired, then purified.

Chloropolysporins B and C are preferably separated from other products in said liquid portion by means of an adsorbent, either by adsorbing the impurities or by adsorbing the chloropolysporins or by adsorbing both separately or together and then eluting the chloropolysporins. A wide range of adsorbents may be used; examples which we have found to be particularly satisfactory include: activated carbon; and adsorbing resins such as Amberlite (registered trade mark) XAD-2, XAD-4 or XAD-7 (products of Rohm and Haas), Diaion (registered trade mark) HP 10, HP 20, CHP 20P or HP 50 (products of Mitsubishi Chemical Industries Co., Ltd.) and polyamide gels (a product of Woelm Pharma, West Germany). The impurities present in the liquid portion may be removed by passing the solution containing the chloropolysporins through a layer or column of one or more of the aforementioned adsorbents or by adsorbing the chloropolysporins on one or more of the adsorbents and then eluting the chloropolysporins, either separately or together, with a suitable eluent. Suitable eluents include mixtures of methanol, acetone or butanol with water.

The chloropolysporins B and C thus obtained may be further purified by various means. Suitable methods include: partition column chromatography using a cellulose product, such as Avicel (a registered trade mark for a product of Asahi Chemical Industry Co., Ltd.) or Sephadex LH-20 (a registered trade mark for a product of Farmacia, Sweden); reverse phase column chromatography using a carrier for the reverse phase; extraction based on the differences in distribution in solvents between chloropolysporins B and C and their contaminating impurities; or the counter-current distribution method. These purification techniques may be used singly or in combination and may, if needed, be repeated one or more times.

Chloropolysporins B and C are preferably separated from each other by chromatography. A preferred system for this purpose is System 500 (a product of Waters Co.), using the Preppack $C_{18}$ cartridge. A suitable eluent is a buffered mixture containing acetonitrile and maintained at a slightly acidic pH value.

Depending upon the culture conditions, chloropolysporins B and C can exist in the mycelium from the culture broth and can be extracted therefrom by conventional techniques. For example, they can be extracted with a hydrophilic organic solvent (such as an alcohol or acetone), and then the solvent removed from the extract to leave a residue, which is dissolved in an aqueous medium. The chloropolysporins can be extracted from the resulting solution and purified as described above.

Chloropolysporins B and C thus obtained have, as their sulfates, the physical and chemical properties described above. They are normally and preferably separated from the culture broth in the form of a water-soluble salt and are most conveniently characterized in the form of such a salt, i.e., as herein, in the form of the sulfate, since chloropolysporins B and C themselves (i.e. the free bases) are insoluble in water.

Since chloropolysporins B and C are amphoteric in character, they form salts and these salts also form part of the present invention. The nature of such salts is not critical, except that, where they are to be used for medicinal or veterinary purposes, they must be medicinally acceptable, i.e. they must not, or must not to a significant extent, either have increased toxicity or have reduced activity, as compared with the free base. Examples of suitable acids for the formation of such salts include: inorganic acids, such as hydrochloric acid, sulfuric acid or phosphoric acid; organic carboxylic acids, such as acetic acid, citric acid, tartaric acid, malonic acid, maleic acid, malic acid, fumaric acid, itaconic acid, citraconic acid or succinic acid; and organic sulfonic acids, such as methanesulfonic acid, benzenesulfonic acid, naphthalenesulfonic acid or p-toluenesulfonic acid.

Where the chloropolysporin B or C is isolated in the form of a salt, it may be converted to the free base by conventional means, such as the use of ion-exchange resins or of adsorbents for reverse phase chromatography. An aqueous solution of a salt will normally have an acidic pH value; adjustment of this pH value to approximate neutrality will result in mainly precipitation of the free base, which may then be collected by suitable means, e.g. filtration or centrifugation. This product will, however, normally be contaminated by impurities, including minor proportions of the relevant salts, and will, therefore, normally require further purification. Accordingly, a more preferred method is by using, for example, a suitable ion-exchange resin or an adsorbent for reverse phase chromatography. These compounds, however, share with known glycopeptide antibiotics, such as avoparcin, the property of being very difficult to isolate in the form of the free base [see e.g. W. J. McGahren et al., Journal of Antibiotics, XXXVI, 12, 1671 (1983)] and they are, accordingly, preferably isolated and employed in salt form.

It is currently believed that chloropolysporins B and C may be represented by the planar structural formula:

medium (produced by Nissui). The results are shown in Tables 3 and 4.

TABLE 3

| Test strain | | MIC (µg/ml) Chloropolysporin | |
|---|---|---|---|
| | | B | C |
| Staphylococcus aureus | FDA 209P JC-1 | 1.56 | 1.56 |
| Staphylococcus aureus | SANK 70175 | 3.13 | 1.56 |
| Staphylococcus aureus | Smith | 12.5 | 6.25 |
| Staphylococcus epidermidis | SANK 71575 | 3.13 | 3.13 |
| Enterococcus faecalis | SANK 71778 | 1.56 | 1.56 |
| Bacillus subtilis | PCI 219 | 0.78 | 0.78 |
| Mycobacterium smegmatis | ATCC 607 | 25.0 | 12.5 |
| Escherichia coli | NIHJ JC-2 | >100 | >100 |
| Klebsiella pneumoniae | PCI 602 | >100 | >100 |
| Pseudomonas aeruginosa | NCTC 10490 | >100 | >100 |
| Serratia marcescens | SANK 73060 | >100 | >100 |
| Proteus mirabilis | SANK 70461 | >100 | >100 |

TABLE 4

| Test strain | MIC (µg/ml) Chloropolysporin | |
|---|---|---|
| | B | C |
| Bacteroides fragilis | >100 | >100 |
| Eubacterium cylindroides | 6.25 | 3.13 |
| Fusobacterium necrophorum | >100 | >100 |
| Peptostreptococcus saccharoliticus | 6.25 | 3.13 |
| Peptostreptococcus parvulus | 0.78 | 0.39 |
| Propionibacterium acnes | 0.78 | 0.39 |
| Clostridium symbiosum | 1.56 | 0.39 |
| Clostridium ramosum | 1.56 | 1.56 |
| Clostridium perfringens | 0.20 | 0.10 |
| Clostridium difficile | 0.78 | 0.39 |

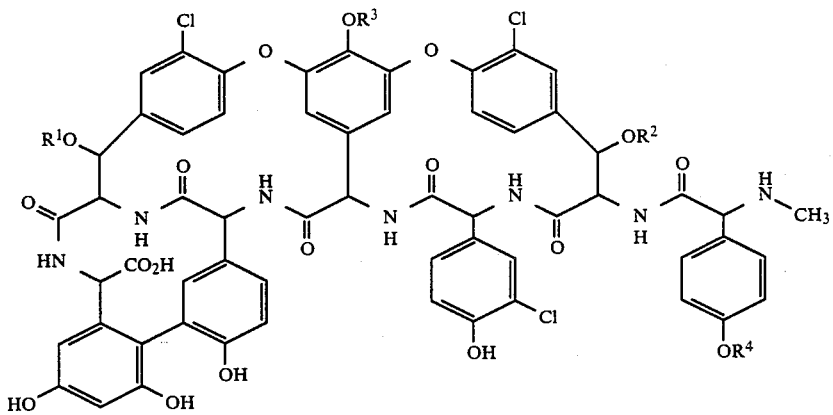

in which:
for chloropolysporin B,
$R^1$ represents a ristosamine residue;
$R^2$ represents a mannose residue;
$R^3$ represents a glucose residue; and
$R^4$ represents a rhamnose residue;
for chloropolysporin C.,
$R^1$ represents a ristosamine residue;
$R^2$ represents a mannose residue;
$R^3$ represents a glucose residue; and
$R^4$ represents a hydrogen atom.

Accordingly, chloropolysporins B and C differ only in the substituent represented by —$OR^4$ in the above formula.

It is probable that the various assymetric carbon atoms shown in the above formula adopt, in chloropolysporins B and C, specific configurations, but these have not, to date, been elucidated.

The minimal inhibitory concentrations (MIC) of chloropolysporins B and C against various gram-positive and gram-negative bacteria were determined by the two-fold agar dilution method, using a Mueller-Hinton agar medium (produced by Difco); the MIC against anaerobic bacteria was determined using a GAM agar From the results given in the above Tables, it can be seen that chloropolysporins B and C are effective against aerobic gram-positive bacteria, such as *Staphylococcus aureus, Staphylococcus epidermidis, Enterococcus faecalis, Bacillus subtilis* and *Mycobacterium smegmatis*, and against anaerobic gram-positive bacteria, such as *Eubacterium cylindroides, Peptostreptococcus saccharoliticus, Propionibacterium acnes, Clostridium symbiosum, Clostridium perfringens* and *Clostridium difficile*.

Comparison of the properties, chemical, physical and biological, given above of chloropolysporins B and C with those of known antibiotics leads to the conclusion that they belong to the class of glycopeptide antibiotics containing chlorine, such as vancomycin, a voparcin α and β, actinoidins A and B or A-35512 B. However, chloropolysporins B and C can be clearly distinguished from these known antibiotics on the basis of the differences shown in the following Table 5. Specifically, they have different neutral saccharide components and different amino acids are produced on acid hydrolysis. Moreover, they move a different distance on high voltage paper electrophoresis (HVPE,3300 volts/60 cm, 1 hour, pH 7.5, in 0.1M tris-hydrochloric acid buffer solution), and they have different chlorine contents.

TABLE 5

| Antibiotic | Neutral saccharide | Amino acid | Distance | Chlorine content (%) |
|---|---|---|---|---|
| Vancomycin | Glucose | Aspartic acid N-methylleucine | | 4.89 |
| Avoparcin α | Glucose, Mannose, Rhamnose | 4-Hydroxyphenyl-glycine, N-methyl-p-hydroxyphenyl-glycine | 9.4 cm | 1.85 |
| Avoparcin β | Glucose, Mannose, Rhamnose | 3-Chloro-4-hydroxy-phenylglycine, N-methyl-p-hydroxy-phenylglycine | 9.4 cm | 3.65 |
| Actinoidin A | Glucose, Mannose | 4-Hydroxyphenyl-glycine, Phenyl-alanine | | 2.02 |
| Actinoidin B | Glucose, Mannose, | 2-Chloro-3-hydroxy-phenylglycine, Phenylalanine | | 3.96 |
| A-35512B | Glucose, Mannose, Rhamnose, Fucose | | | 1.82 |
| Actaplanin | Glucose, Mannose Rhamnose | | | 1.96 |
| Ristocetin A | Glucose, Mannose Rhamnose Arabinose | | | 0 |
| Ristocetin B | Glucose, Mannose, Rhamnose | | | 0 |
| Chloropolysporin B | Glucose, Mannose, Rhamnose | 3-Chloro-4-hydroxyphenyl-glycine, N-methyl-p-hydroxyphenyl-glycine | 4 cm | 5.11 |
| Chloropolysporin C | Glucose, Mannose | 3-Chloro-4-hydroxyphenyl-glycine, N-methyl-p-hydroxy-phenylglycine | 4 cm | 5.62 |

The value reported above as "Distance" is the distance of movement on high voltage paper electrophoresis, measured using bioautography with *Bacillus subtilis* PCI 219 as the test organism.

From the above findings, it can be seen that chloropolysporins B and C can be used as antibiotics against various diseases caused by bacterial infections. The route of administration can vary widely and may be parenteral (e.g. by subcutaneous, intravenous or intramuscular injection or by suppository) or oral (in which case it may be in the form of a tablet, capsule, powder or granule). The dose will, of course, vary with the nature of the disease to be treated, the age, condition and body weight of the patient and the route and time of administration; however, for an adult human patient, a daily dose of from 0.1 to 1.0 grams is preferred and this may be administered in a single dose or in divided doses.

Moreover, in view of the strong activity of chloropolysporins B and C against infectious bacteria of the genus Clostridium, they can be expected to be valuable growth-promoting agents for veterinary use. Bacteria of the genus Clostridium, particularly *Clostridium perfringens* and *Clostridium difficile*, are often present in the intestines of farm animals and are the cause of diarrhoea. Since chloropolysporins B and C have a strong activity against such microorganisms, they would suppress the growth of such microorganisms in the intestines and thus improve the microbial balance of the intestines. This, in turn, would improve feed efficiency, thus contributing to weight gain and improved milk production in various farm animals, including ruminants, pigs and poultry. Moreover, chloropolysporins B and C, in common with the other glycopeptide antibiotics, are likely to have a low rate of absorption through the digestive organs and, as a result, where the chloropolysporin B or C is administered in the feed, little will remain in the animal body and hence in animal products, such meat, milk or eggs. When the chloropolysporin B or C is used as a growth-promoting agent for animals, it is preferably administered orally. Although it may be formulated into an edible composition with any suitable carrier or diluent, it is particularly convenient to administer it in admixture with an animal feed or with drinking water. When the chloropolysporin B or C is used as a feed additive, it may be mixed alone with the feed or it may be mixed in combination with other non-toxic edible excipients, nutrient supplements (e.g. vitamins, minerals or amino-acids), other antibiotics, anticoccidial agents or enzymes. For administration to animals as a growth-promoting agent, the chloropolysporin B or C need not necessarily be in a completely purified form and it may be used in a crude or partially purified form, as obtained at any desired stage during the extraction and purification described above. For use as a growth-promoting agent, chloropolysporin B or C is preferably employed in an amount of from 1 to 200, more preferably from 5 to 60, ppm by weight on the basis of the feed, drinking water or other carrier to which it is added; where an impure form of chloropolysporin B or C is employed, a concentration having equivalent activity is used.

Animals to which chloropolysporin B or C can be administered include farm mammals (e.g. cattle, horses, swine, sheep and goats), poultry (e.g. chickens, turkeys and ducks) and pet animals (e.g. dogs, cats and birds). Most significantly, when chloropolysporin B or C is administered orally to animals, their growth is effectively promoted, but it is little absorbed from the gastrointestinal tract and it exhibits low retention in animal tissues: thus, there is an almost complete absence of chloropolysporin B or C residues in the products (e.g. milk, meat or eggs) of animals to which it has been administered, which is a great advantage from the view point of food hygiene.

The invention is further illustrated by the following examples.

EXAMPLE 1

PREPARATION OF CHLOROPOLYSPORINS B AND C

One loopful growth of Micropolyspora sp. SANK 60983 was inoculated into a 500 ml Erlenmeyer flask containing 80 ml of medium A, which has the following composition (percentages are by weight):

| MEDIUM A | |
|---|---|
| Glucose | 3% |
| Pressed yeast | 1% |
| Soybean meal | 3% |

-continued

| MEDIUM A | |
|---|---|
| Calcium carbonate | 0.4% |
| Magnesium sulfate | 0.2% |
| Anti-foaming agent (Nissan CB-442) | 0.01% |
| Water (adjusted to pH 7.0) | the balance |

The microorganism was then cultured for 84 hours at 28° C., using a rotary shaker at 220 r.p.m.

25 ml of the resulting seed culture were inoculated into each of four 2 liter Erlenmeyer flasks, each containing 500 ml of medium B, which has the following composition. (percentages are by weight):

| MEDIUM B | |
|---|---|
| Glucose | 5% |
| Yeast extract | 0.1% |
| Soybean meal | 1% |
| Polypepton (a product of Daigo Eiyo Co. Ltd., Japan) | 0.4% |
| Beef extract | 0.4% |
| Sodium chloride | 0.25% |
| Calcium carbonate | 0.5% |
| Anti-foaming agent (Nissan CB-442) | 0.01% |
| Water (adjusted to pH 7.2) | the balance |

The microorganism was then cultured at 28° C. for 24 hours, using a rotary shaker at 220 r.p.m.

The resulting cultured broths were combined. 750 ml of this broth were then inoculated into each of two 30 liter jar fermentors, each containing 15 liters of medium B, and the microorganism was then cultured at 28° C. for 69 hours, whilst aerating at the rate of 15 liters per minute and stirring.

At the end of this time, batches of cultured broth separately cultivated as described above were combined to give a total of 30 liters of cultured broth. Celite 545 (a registered trade mark for a product of Johns-Manville Products Corp, New Jersey, U.S.A.) filter aid was added to the cultured broth and the mixture was filtered, to give 30 liters of a filtrate. This filtrate was adsorbed on 3 liters of Diaion HP 20 (a product of Mitsubishi Chemical Industries Co., Ltd.), and the adsorbent was washed with water and then eluted with 50% v/v aqueous acetone. Acetone was evaporated from the combined active fractions by evaporation under reduced pressure; and the concentrate thus obtained was lyophilized, giving 44 g of a crude powder.

41 g of this powder were dissolved in water and adsorbed onto 1.8 liters of Diaion HP 20, washed with 5 liters of water and 2 liters of 10% v/v aqueous acetone, and then eluted with 4 liters of 50% v/v aqueous acetone. The active fractions from the elution were collected and condensed to a volume of 1 liter by evaporation under reduced pressure. The condensate was centrifuged at 5000 r.p.m. and the resulting precipitate was dried, to give 9.6 g of crude powder containing chloropolysporins B and C.

This crude powder was dissolved in 1 liter of 50% v/v aqueous methanol and then adsorbed onto 200 ml of acidic alumina (a product of Woelm Pharma, West Germany), which had previously been equilibrated with 50% v/v aqueous methanol. The adsorbed product was then eluted with the same solvent, and the active fractions, a total of 1.1 liters, were collected. The combined active fractions were passed through 60 ml of Dowex 21 K (OH⁻), and eluted with water. The active fractions from this elution, a total volume of 1.2 liters, were collected and then condensed by evaporation under reduced pressure to a volume of 30 ml. This condensate was lyophilized, to give 1.23 g of powder. The powder was dissolved in aqueous hydrochloric acid of pH 4.0 and then adsorbed onto 56 g of Polyamide filled with water (a product of Woelm Pharma, West Germany). This was subjected to gradient elution with 400 ml of water and 1.2 liters of methanol, in 20 ml fractions, up to fraction 80. Fractions 30-60 were collected and combined. The methanol was distilled off under reduced pressure and the resulting concentrate was lyophilized, to give 738 mg of a white powder containing chloropolysporins B and C.

4.4 g of this crude white powder containing chloropolysporins B and C were dissolved in 80 ml of a mixed solvent consisting of 15 parts of acetonitrile and 85 parts of a buffer solution (containing 0.2% w/v sodium heptanesulfonate, 2.5% w/v acetic acid and 0.5% w/v concentrated aqueous ammonia); the solution was then adsorbed on a System 500 chromatography system (a product of Waters Co), using a Preppack $C_{18}$ cartridge. This was developed and eluted with the same mixed solvent as mentioned above at a flow rate of 100-150 ml per minute. Chloropolysporin B was eluted in the solvent after between 800 ml and 1700 ml of the eluant had passed through the cartridge, whilst chloropolysporin C was eluted after between 1700 and 4700 ml of the eluant had passed.

The active fractions containing chloropolysporin B were collected and adjusted to a pH value of 7.0. They were then concentrated by evaporation under reduced pressure, to distill off the acetonitrile. The resulting concentrated solution was adsorbed on a Diaion HP 20 column (100 ml), washed with water, and then eluted with 500 ml of 70% v/v aqueous acetone. The eluate was condensed by evaporation under reduced pressure, and the residue was lyophilized to afford chloropolysporin B heptanesulfonate as a powder.

200 mg of this powder were dissolved in 5 ml of water, and then 1 ml of a 10% w/v aqueous solution of sodium dodecylsulfate was dropped into the resulting solution. The precipitate which formed was collected by centrifugation at 3000 rpm for 10 minutes. This precipitate was suspended in water and the suspension was again centrifuged at 3000 rpm for 10 minutes to wash the precipitate. This operation was repeated a further three times to wash the precipitate. The precipitate was then dissolved in 3 ml of methanol and the insoluble residue was filtered off. 2 ml of a 0.5M methanolic solution of triethylamine sulfate were added dropwise and the resulting precipitate was collected by centrifugation at 3000 rpm for 10 minutes. This precipitate was suspended in a small amount of methanol and again centrifuged at 3000 rpm for 10 minutes. This was repeated a further three times to wash the precipitate. The precipitate was then dissolved in 1.5 ml of water and the insoluble residue was filtered off. Lyophilization of the filtrate gave 65 mg of chloropolysporin B sulfate.

The active fractions containing the chloropolysporin C were collected and adjusted to a pH value of 7.0. They were then concentrated by evaporation under reduced pressure to distill off the acetonitrile, and the concentrate was absorbed on a Diaion HP 20 column (50 ml), washed with water, and then eluted with 300 ml of 70% v/v aqueous acetone. The eluate was condensed by evaporation under reduced pressure, and the residue was lyophilized to afford 1.0 g of a powder containing chloropolysporin C heptanesulfonate. This powder was dissolved in 10 ml of a mixed solvent consisting of 15 parts of acetonitrile and 85 parts of a buffer solution (containing 0.2% w/v sodium heptanesulfonate, 2.5% w/v acetic acid and 0.5% w/v concentrated aqueous ammonia) and each 2 ml of the resulting solution was adsorbed on a Lobar column RP-18 (size B, a product of Merck and Co). This was developed and eluted at 13 ml per minute with the same mixed solvent, and the chloropolysporin C was eluted 30-40 minutes after commencement of the elution, whilst the contaminating chloropolysporin B was eluted between 18 and 20 minutes. This operation was repeated a total of 5 times.

The chloropolysporin C fractions were collected and adjusted to a pH value of 5.8. They were then concentrated by evaporation under reduced pressure. The concentrate was adsorbed onto 40 ml of Diaion HP 20, washed with water and eluted with 200 ml of 50% v/v aqueous acetone. The eluate was condensed by evaporation under reduced pressure, and the residue was lyophilized, to give 250 mg of a crude chloropolysporin C-containing powder. This powder was dissolved in 5 ml of 50% v/v aqueous methanol, and the solution was adsorbed on 150 ml of Toyopearl HW40F (a product of Toyo Soda Co Ltd), which had previously been equilibrated with 50% v/v aqueous methanol. The column was developed and eluted with 50% v/v aqueous methanol at a flow rate of 0.6 ml per minute. The eluate was collected in fractions of 2.5 ml each, and the chloropolysporin C heptanesulfonate was found to be present in fractions 51-64.

These fractions were combined and then condensed under reduced pressure, and then 1 ml of a 10% w/v aqueous solution of sodium dodecylsulfate was added dropwise. The resulting precipitate was collected by contrifugation at 3000 rpm for 10 minutes. The precipitate was then suspended in water and washed by centrifugation at 3000 rpm for 10 minutes. These operations were repeated a further three times. The precipitate was then dissolved in 3 ml of methanol and the insoluble residue was filtered off. 2 ml of a 0.5M methanolic solution of triethylamine sulfate were then added dropwise to the filtrate and the resulting precipitate was collected by centrifugation at 3000 rpm for 10 minutes. This precipitate was suspended in methanol and washed by centrifugation at 3000 rpm for 10 minutes. This operation was repeated a further three times. The resulting precipitate was dissolved in 1.5 ml of water, the insoluble residue was removed, and the solution was lyophilized to afford 54 mg of chloropolysporin C sulfate.

The chloropolysporin B sulfate and chloropolysporin C sulfate obtained as described above had the properties heretofor described.

EXAMPLE 2

1 loopful growth of Micropolyspora sp. SANK 60983 was inoculated into a 500 ml Erlenmeyer flask containing 80 ml of medium A, having the composition described in Example 1. It was then cultivated at 28° C. for 72 hours, using a rotary shaker at 220 rpm. 25 ml of this seed culture were inoculated into each of six 2 liter Erlenmeyer flasks, each containing 500 ml of medium B, having the composition described in Example 1, and cultivated for 24 hours at 28° C.

The whole of the cultured broth was then inoculated into a 100 liter tank containing 60 liters of medium B and cultivated at 28° C. for a further 24 hours.

15 liters of the resulting seed culture were then inoculated into each of two 600 liter tanks, each containing 300 liters of medium B, and the microorganism was cultivated, whilst stirring, for 67 hours at 28° C., with aeration at the rate of 300 liters per minute, with an internal pressure of 1.0 kg/cm$^2$ and with 3-5 ppm of dissolved oxygen.

At the end of the cultivation period, a Celite 545 filter aid was added to the culture and the culture was filtered, to afford 550 liters of filtrate. This filtrate was passed through a Diaion HP 20 column (60 liters) to adsorb the chloropolysporin B. The column was washed with water and eluted with 50% v/v aqueous acetone, yielding 570 liters of active fractions. The acetone was then distilled off under reduced pressure, leaving 280 liters of a concentrate. This concentrate was extracted twice, each time with 200 liters of butanol to remove the impurities, and the residual aqueous layer was condensed to 5 liters by evaporation under reduced pressure. The concentrated solution was adjusted to a pH value of 5.8 by the addition of 1N aqueous sodium hydroxide, and then the solution was adsorbed on a column containing 4.2 liters of Polyamide gel (a product of Woelm Pharma, West Germany), and developed and eluted with water. The eluate was separated in fractions of 1 liter each, and chloropolysporin B was eluted in fractions 3-9. These fractions were combined, and adjusted to a pH value of 4.0 by the addition of 1N aqueous hydrochloric acid. The resulting 7 liters of active fractions were condensed by evaporation under reduced pressure, and the residue was lyophilized, to give 42 g of chloropolysporin B hydrochloride.

Elemental analysis: Calculated for $C_{83}H_{89}O_{34}N_8Cl_3.0.5HCl.4H_2O$: C, 51.41%; H, 5.07%; N, 5.78%; Cl, 6.40%. Found: C, 51.05%; H, 5.37%; N, 6.36%; Cl, 6.90%.

Following the same procedure as described in Example 2, but employing the chloropolysporin C-containing fractions, chloropolysporin C hydrochloride was also produced.

Elemental analysis: Calculated for $C_{77}H_{79}O_{30}N_8Cl_3.HCl.9H_2O$: C, 48.64%; H, 5.19%; N, 5.89%; Cl, 7.45%. Found: C, 48.48%; H, 5.13%; N, 5.81%; Cl, 7.78%.

EXAMPLE 3

CAPSULES FOR ORAL USE

The following ingredients were mixed:

| | |
|---|---|
| Chloropolysporin B hydrochloride | 100 mg |
| Lactose | 100 mg |
| Corn starch | 148.5 mg |
| Magnesium stearate | 1.5 mg |

The mixture was sieved through a 30 Tyler standard mesh sieve, giving 350 mg of a fine powder, which was put into a No. 2 gelatin capsule.

EXAMPLE 4

The procedure described in Example 3 was repeated, except that chloropolysporin C hydrochloride was employed in place of chloropolysporin B hydrochloride.

Figure 4:
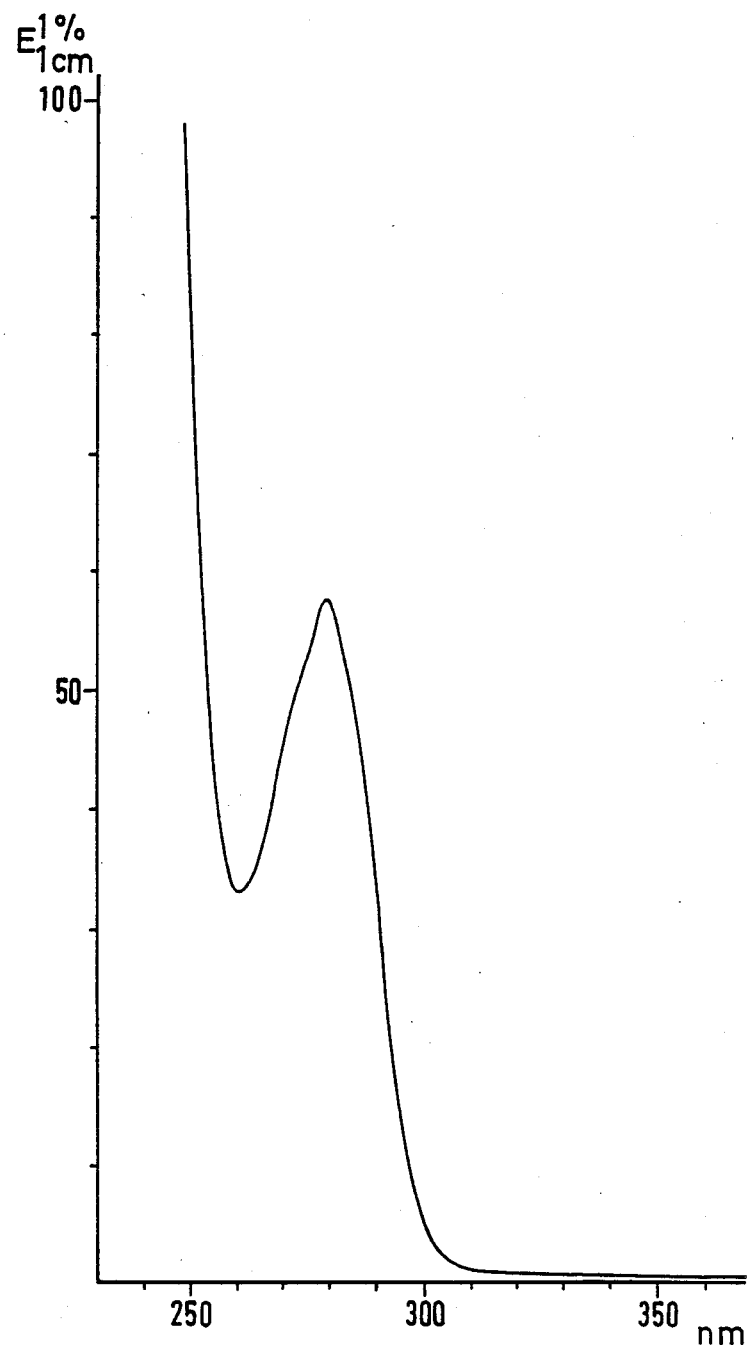
FIG. 4 is the ultraviolet absorption spectrum of chloropolysporin C.
Figure 5:
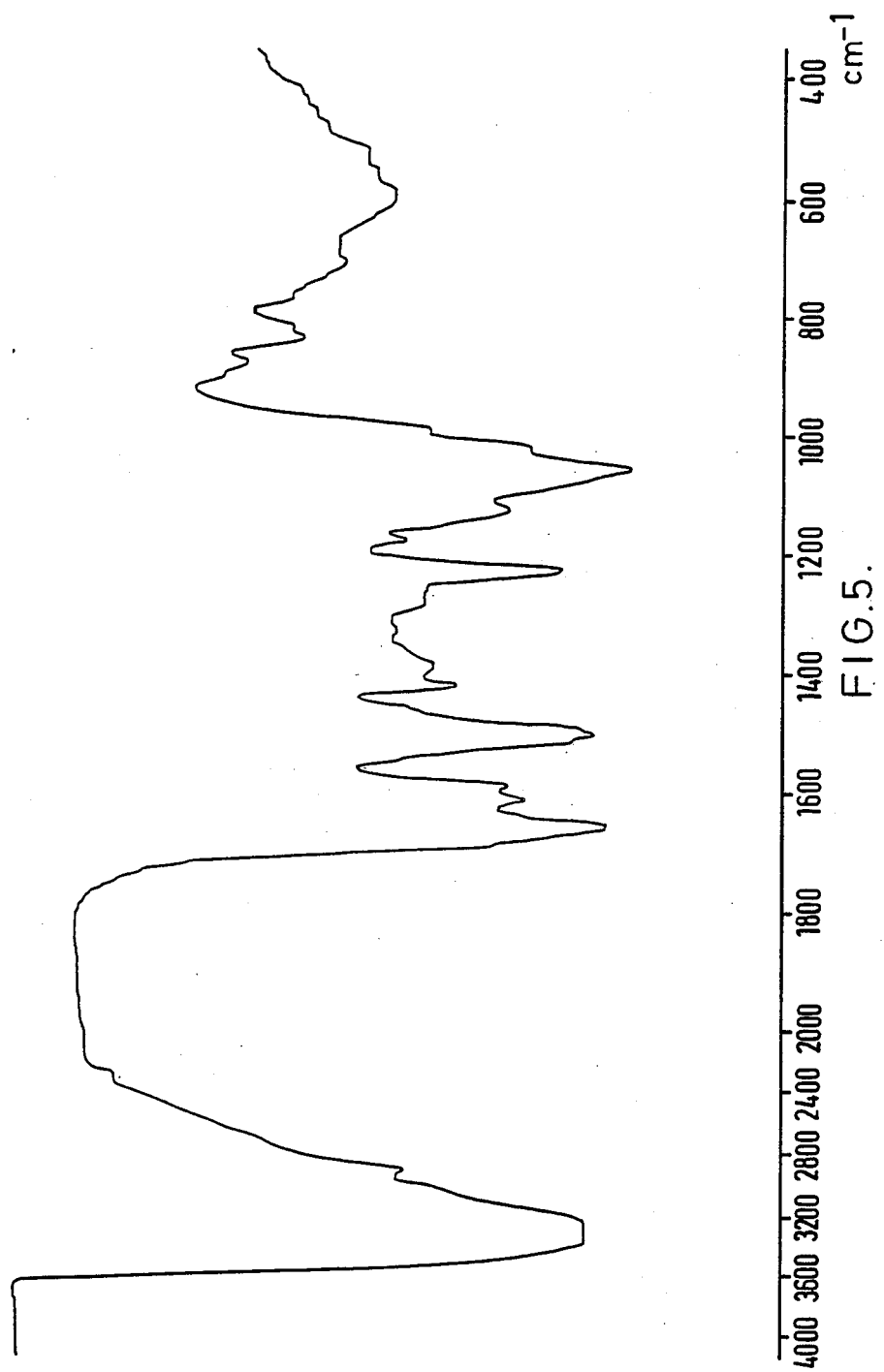
FIG. 5 is the infrared absorption spectrum of chloropolysporin C.
Figure 6:
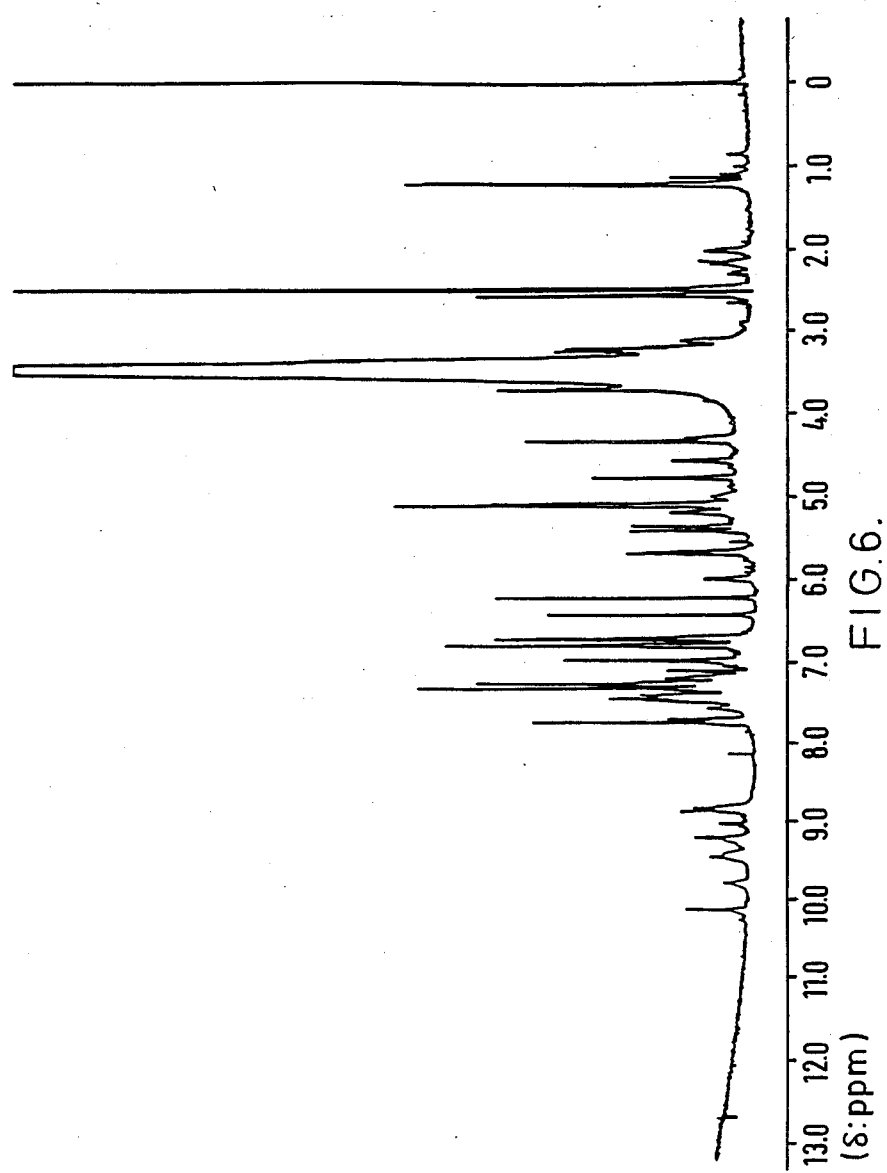
FIG. 6 is the NMR spectrum of chloropolysporin C.

We claim:
1. An antibiotic substance named chloropolysporin C and pharmaceutically acceptable salts thereof, which, as its sulfate, is characterized by the following properties:

(a) it takes the form of an amphoteric white powder, soluble in water;
(b) specific rotation: $[\alpha]^{25} -64.4°$ (C=1.08, 0.1N aqueous hydrochloric acid, sodium D-line);
(c) elemental analysis: C, 50.53%; H, 4.69%; N, 6.14%; Cl, 5.62%; S, 1.12%;
(d) on acid hydrolysis it yields: neutral saccharides: glucose and mannose; amino acids: 3-chloro-4-hydroxyphenylglycine and N-methyl-p-hydroxyphenylglycine;
(e) ultraviolet absorption spectrum: as illustrated in FIG. 4 of the accompanying drawings, having an absorption maximum $\lambda_{max}$ at 280 nm ($E_{1cm}=57$) in a 0.1N solution of hydrochloric acid, the absorbence, E, being measured at a concentration of 1% w/v;
(f) infrared absorption spectrum: the infrared absorption spectrum ($\nu cm^{-1}$) measured on a KBr disc is as shown in FIG. 5 of the accompanying drawings;
(g) nuclear magnetic resonance spectrum: the nuclear magnetic resonance spectrum ($\delta$ ppm), measured at 400 MHz in deuterated dimethyl sulfoxide using tetramethylsilane as the internal standard, is as illustrated in FIG. 6 of the accompanying drawings;
(h) solubility: soluble in water and methanol, sparingly soluble in acetone, and insoluble in ethyl acetate, chloroform and benzene;
(i) color reactions: positive in Ninhydrin and Rydon-Smith reactions;
(j) thin layer chromatography: Rf value=0.65, using a cellulose sheet (Eastman) as adsorbent and a 15:10:3:12 by volume mixture of butanol, pyridine, acetic acid and water as the developing solvent;
(k) molecular formula: $C_{77}H_{79}O_{30}N_8Cl_3.0.5H_2SO_4.5H_2O$;
(l) molecular weight: the molecular weight, measured by FAB-MS, was 1700 (MH+, 1701).

2. A compound of the formula:

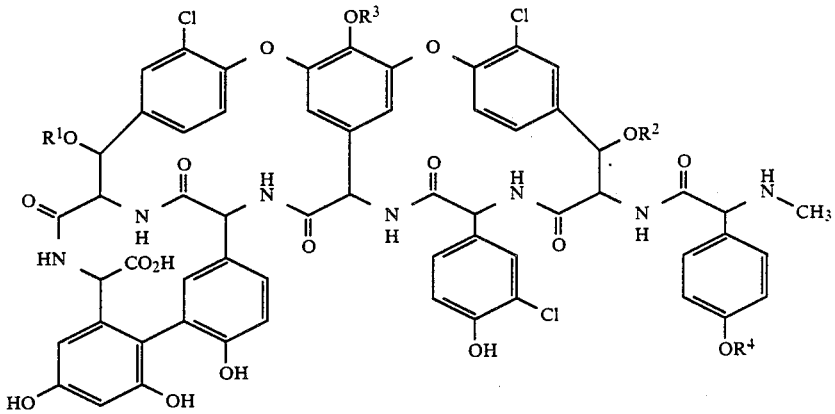

wherein:
$R^1$ represents a ristosamine residue;
$R^2$ represents a mannose residue;
$R^3$ represents a glucose residue; and
$R^4$ represents a hydrogen atom;
or a pharmaceutically acceptable salt thereof.

3. A pharmaceutical or veterinary composition comprising the antibiotic substance chloropolysporin C or a salt thereof in an antibiotic effective amount as defined in claim 1 in admixture with a pharmaceutical or veterinary carrier or diluent.

4. An antibiotic composition comprising 0.1 to 1.0 grams of the chloropolysporin C or salt thereof of claim 1 in a pharmaceutical carrier or diluent.

5. A method for the treatment or prophylaxis of bacterial infections by administering an antibiotic effective amount the antibiotic substance chloropolysporin C or a salt thereof as defined in claim 1 to an animal.

6. A method of promoting the growth of a farm animal by the oral administration of an effective amount of the antibiotic substance chloropolysporin C or a salt thereof as defined in claim 1 to said animal.

* * * * *